United States Patent
Laing et al.

(10) Patent No.: US 9,076,187 B1
(45) Date of Patent: Jul. 7, 2015

(54) MEDICAL DEVICE PAYMENT SYSTEM

(71) Applicant: Advanced Uro-Solutions, LLC, Elizabethton, TN (US)

(72) Inventors: Brent Laing, Elizabethton, TN (US); John Green, Elizabethton, TN (US)

(73) Assignee: Advanced Uro-Solutions, LLC, Minneapolis, MN (US)

( * ) Notice: Subject to any disclaimer, the term of this patent is extended or adjusted under 35 U.S.C. 154(b) by 0 days.

(21) Appl. No.: 14/453,844

(22) Filed: Aug. 7, 2014

Related U.S. Application Data

(60) Continuation-in-part of application No. 14/298,207, filed on Jun. 6, 2014, which is a continuation of application No. 14/149,310, filed on Jan. 7, 2014, now Pat. No. 8,818,520, which is a division of application No. 13/523,965, filed on Jun. 15, 2012, now Pat. No. 8,660,646.

(60) Provisional application No. 61/978,517, filed on Apr. 11, 2014, provisional application No. 61/497,570, filed on Jun. 16, 2011.

(51) Int. Cl.
*A61N 1/00* (2006.01)
*G06Q 50/22* (2012.01)
*G06Q 20/14* (2012.01)
*G06Q 20/28* (2012.01)
*G06Q 20/24* (2012.01)

(52) U.S. Cl.
CPC ............ *G06Q 50/22* (2013.01); *G06Q 20/14* (2013.01); *G06Q 20/28* (2013.01); *G06Q 20/24* (2013.01); *A61H 2201/5035* (2013.01)

(58) Field of Classification Search
USPC ....................... 607/39–44, 59, 144
See application file for complete search history.

(56) References Cited

U.S. PATENT DOCUMENTS

| | | | |
|---|---|---|---|
| 5,258,906 A | 11/1993 | Kroll et al. | |
| 6,049,789 A | 4/2000 | Frison et al. | |
| 6,493,588 B1 | 12/2002 | Malaney et al. | |
| 6,662,052 B1 | 12/2003 | Sarwal et al. | |
| 6,829,704 B2 | 12/2004 | Zhang et al. | |
| 6,966,000 B2 | 11/2005 | Zhang et al. | |
| 6,983,375 B2 | 1/2006 | Zhang et al. | |
| 6,990,434 B2 | 1/2006 | Minogue et al. | |
| 7,093,032 B2 | 8/2006 | Minogue et al. | |
| 7,113,894 B2 | 9/2006 | Minogue et al. | |
| 7,219,222 B1 | 5/2007 | Durbin et al. | |
| 7,349,856 B2 | 3/2008 | Ackermann et al. | |
| 7,421,516 B2 | 9/2008 | Minogue et al. | |
| 7,536,226 B2 | 5/2009 | Williams et al. | |
| 7,634,645 B2 | 12/2009 | Zhang et al. | |
| 7,739,725 B1 | 6/2010 | Zhang et al. | |
| 7,813,809 B2 | 10/2010 | Strother et al. | |
| 7,962,416 B1 | 6/2011 | Durbin et al. | |
| 2002/0120467 A1 | 8/2002 | Buanes | |

(Continued)

*Primary Examiner* — Nicole F Lavert

(57) ABSTRACT

Methods of providing payment for use of a medical device on a per-treatment session basis are disclosed. The methods include downloading treatment credits to the device linked to a customer account and activating the medical device when the number of available treatment credits is greater the one. The number of treatment credits downloaded to the device is based on at least one of a credit limit provided to the customer account and a number of prepaid treatment credits purchased by the customer. In other embodiments, the medical device monitors the number of treatment sessions performed and activates the device only when a customer's account is current.

18 Claims, 7 Drawing Sheets

(56) References Cited

U.S. PATENT DOCUMENTS

| | | |
|---|---|---|
| 2004/0215287 A1 | 10/2004 | Swoyer et al. |
| 2005/0165693 A1 | 7/2005 | Moritzen |
| 2006/0190048 A1 | 8/2006 | Gerber |
| 2008/0140451 A1 | 6/2008 | Hedrick et al. |
| 2008/0221644 A1 | 9/2008 | Vallapureddy et al. |
| 2008/0300449 A1 | 12/2008 | Gerber et al. |
| 2009/0132018 A1 | 5/2009 | DiUbaldi et al. |
| 2009/0248578 A1 | 10/2009 | Pollock et al. |
| 2010/0114259 A1 | 5/2010 | Herregraven et al. |
| 2011/0172498 A1 | 7/2011 | Olsen et al. |

MEDICAL DEVICE PAYMENT SYSTEM

CROSS-REFERENCE TO RELATED APPLICATIONS

This application claims benefit as a non-provisional of U.S. Patent Application Ser. No. 61/978,517 filed Apr. 11, 2014, entitled "Medical Device Payment System," and as a continuation-in-part of U.S. patent application Ser. No. 14/298,207 filed Jun. 6, 2014, entitled "Percutaneous Tibial Nerve Stimulator," which is a continuation of U.S. patent application Ser. No. 14/149,310 filed Jan. 7, 2014, entitled "Percutaneious Tibial Nerve Stimulator," which is a divisional of U.S. patent application Ser. No. 13/523,965 filed Jun. 15, 2012, entitled "Percutaneous Tibial Nerve Stimulator," and granted as U.S. Pat. No. 8,660,646, which claims priority to U.S. Provisional Application Ser. No. 61/497,570 filed Jun. 16, 2011, and entitled "Percutaneous Tibial Nerve Stimulator," the contents of each being incorporated by reference herein in their entireties.

FIELD

This disclosure relates to the field of payment systems for medical devices and equipment. More particularly, this disclosure relates to a system for providing payment for use of a medical device, particularly dental, veterinary, and nerve stimulator devices, on a per-treatment session basis.

BACKGROUND

Nerve and muscle stimulation are used to treat a variety of medical conditions such as to reduce pain and to assist muscle and joint rehabilitation. Nerve stimulation has also been used for decades to control bladder function. Today, nerve stimulation is used to manage dysfunctions of the central nervous system as well as end organ dysfunction through modulation of relevant peripheral nerve activity. Various approaches to gastrointestinal and bladder neuromodulation have been studied with stimulation of the vagus, pudendal, sacral, and tibial nerves that have proven to be effective in controlling end organ function.

One problem distributing medical devices is that the manufacturers of the devices have trouble implementing into the sale of the devices a financially viable and profitable business model. This is particularly true with respect to medical devices that do not require specialized replacement parts associated with each use. In most cases, devices of this type are sold with all revenue frontloaded into the original sale of the device. The medical provider, office or hospital must pay for all future use of the device on the day of purchase. In other words, the manufacture sells the device to a healthcare customer for a fixed price and then receives no additional income from the customer once the device is sold unless the customer purchases another device. Such devices are numerous and include, for example, nerve stimulating systems, muscle stimulating devices, laser-therapy devices and other radiologic, sonographic, fetal monitoring, diagnostic and therapeutic devices, both clinical and laboratory in nature.

In order for a manufacturer to realize, financially, the lifetime value of any medical device, that value is typically paid at the time of sale of the device. This creates a notable burden of the end user to prepay a sizable percentage of the revenue hoped to be generated by the delivery of services with that device. Rising prices and an uncertain economy has created real obstacles to the purchase of new and effective medical devices. One solution has been for manufacturers to design and incorporate non-reusable components into newer devices to generate ongoing revenue, allowing the original cost of the device to be set at a lower price point. The balance is replaced by the ongoing sales of the non-reusable items by the manufacturer to the end user. For example, U.S. Pat. No. 7,536,226 and U.S. Pat. No. 8,046,082 relate to a nerve stimulation device for treating incontinence where a reusable lead wire system as described in U.S. Pat. No. 6,493,588 was converted into a single lead use system. In other words, manufacturers have resorted to creating specialized replacement parts even when none are necessary in an attempt to artificially create a recurring revenue stream from the sale of the device. However, this results in unnecessary waste when the non-reusable components could be designed to be longer lasting. Additionally, the manufacturer runs the risk of competitors entering the market with their own replacement components for the manufacturer's device.

What is needed therefore is a payment system that can be easily incorporated into medical devices providing the ability to charge a healthcare provider/device owner for each treatment session. This allows a lower initial sale price of the device that is supplemented with a recurring revenue stream so long as the device is used. The purchaser of the device also is benefited with lower initial costs, simplifying their own financials, stretching out payment for and allowing greater access to new technology. The purchaser is provided the ability to pay for the device with revenue actually generated by the device usage. The patients benefit by greater access to new therapies or therapy delivered by newer, more effective or more efficient devices.

Additionally, owners of certain devices may wish to implement the payment system into existing devices to recoup their investment in the device and provide a simple and efficient payment system for their patients.

SUMMARY

According to one embodiment of the disclosure, a method of providing payment for use of a medical device on a per-treatment session basis includes providing a customer computer system having a customer interface; providing a medical device computing unit including a microcontroller for monitoring a number of treatment sessions available to the medical device and for activating the medical device when the number of treatment sessions available is at least one, the number of treatment sessions available determined based on at least one of a credit limit provided to the customer for postpaid treatment sessions and a number of prepaid treatment credits purchased by the customer; receiving a treatment credit request transmitted through the customer interface, the treatment credit request having purchase information including at least one of payment of a number of postpaid treatment sessions already performed and payment for a number of prepaid treatment credits; transmitting the treatment credit request from the customer computer system to a central payment server for validation; receiving at the customer computer system validation information, the validation information corresponding to at least one of the number of postpaid treatment sessions paid for and the number of prepaid treatment credits purchased; connecting the microcontroller of the medical device computing unit to the customer computer system; transmitting the validation information from the customer computer system to the microcontroller; and adjusting the number of treatment sessions available to the medical device based on the validation information.

In certain embodiments, the method further includes determining whether the number of treatment sessions available is at least one and activating the medical device based on a treatment session request when it is determined that the number of treatment sessions available is at least one. The method may also include transmitting usage information from the microcontroller to the customer computer system, the usage information including a number of treatment sessions performed; monitoring the usage information of the medical device through the customer computer system; and providing the usage information to the customer through the customer interface of the customer computer system.

According to some embodiments, the microcontroller communicates with the customer computer system through one of radio frequency, Bluetooth, infrared, and a wireless Internet connection. The microcontroller may also communicate with the customer computer system through a universal serial bus connection.

According to certain embodiments, the medical device includes the customer interface of the customer computer system and a communicator to communicate directly with the central payment server.

According to another embodiment of the disclosure, a method of providing payment for use of a medical device on a per-treatment session basis includes providing a customer computer system having a customer interface; linking the medical device to a customer account, the customer account for monitoring a number of treatment sessions available to the customer account; providing a medical device computing unit including a microcontroller for monitoring usage information directed to a number of treatment sessions performed by the medical device, for updating a number of treatment credits available to the medical device based on the number of treatment sessions performed by the medical device, and for activating the medical device upon a treatment session request when the number of treatment credits available to the medical device is at least one; connecting the medical computing unit to the customer computer system for transmitting at least one of the number of treatment sessions available to the customer account to the microcontroller, each of the number of treatment sessions available transmitted to the microcontroller corresponding to one treatment credit available to the medical device; and updating the number of treatment credits available to the medical device based on the number of treatment sessions available to the microcontroller transmitted from the customer account.

According to certain embodiments, the method further includes receiving a treatment credit request transmitted through the customer interface, the treatment credit request including payment for a number of prepaid treatment credits, each prepaid treatment credit corresponding to one treatment session available to the customer account.

According to certain embodiments, the linking stem further includes linking a credit limit to the customer account, the credit limit providing a number of postpaid treatment credits available to the customer account, each postpaid treatment credit corresponding to one treatment session available to the customer account. The method may also include receiving payment information including payment of at least a portion of the postpaid treatment credits and updating the number of treatment sessions available to the customer account based on the payment information.

According to yet another embodiment, a method for providing payment for use of a medical device on a per-treatment session basis includes providing a computer system having a customer interface and a central payment server; linking the medical device to a customer account; providing the medical device with a medical device computing unit including a microcontroller for monitoring usage information directed to a number of treatment sessions performed by the medical device and a communicator for communicating with the computer system; providing a user with a time certificate having an expiration date, the time certificate operable to be transmitted to the microcontroller, and the microcontroller operable to be activated upon an activation request based on the expiration date of the time certificate; receiving at the computer system the usage information from the medical device computing unit; billing the customer account for the number of treatment sessions performed by the medical device; and updating the expiration date of the time certificate based on receiving payment for the number of treatment sessions performed by the medical device.

BRIEF DESCRIPTION OF THE DRAWINGS

Further advantages of the disclosure are apparent by reference to the detailed description in conjunction with the figures, wherein elements are not to scale so as to more clearly show the details, wherein like reference numbers indicate like elements throughout the several views, and wherein.

DETAILED DESCRIPTION

Referring to FIGS. 1-7, a payment system according to the present disclosure is exemplified with a nerve stimulator device 10 for treating incontinence. It should be understood that the payment system could be implemented into other types of medical devices associated with medical therapy or diagnosis in a similar fashion and as more broadly described in FIGS. 8-9.

Figure 1:
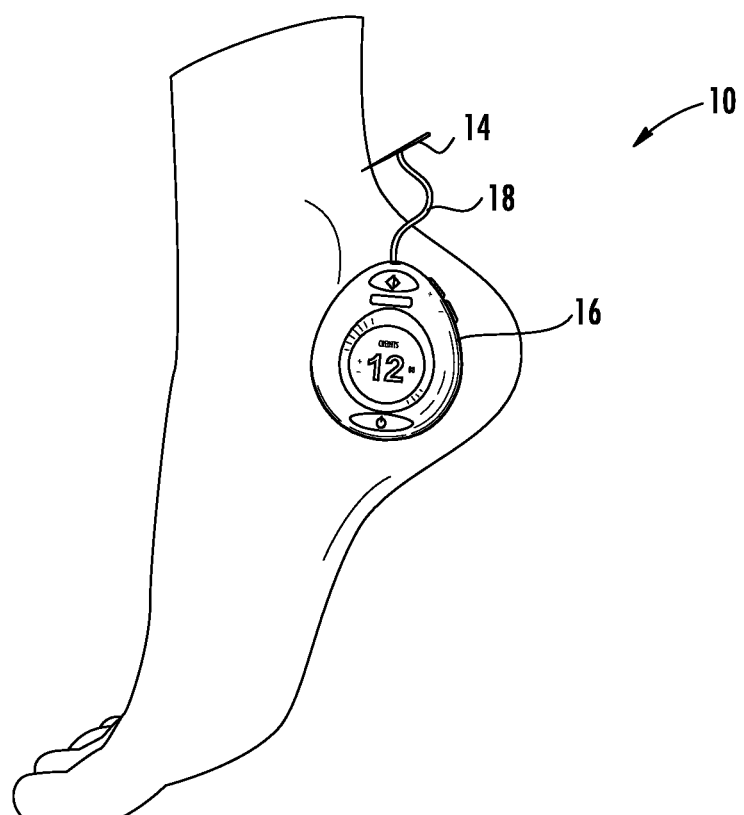
FIG. 1 is a view of the tibial nerve stimulation device applied to the patient according to one embodiment of the disclosure.

As shown in FIG. 1, nerve stimulator device 10 includes a transcutaneous electrode pad (shown in FIG. 4), a percutaneous needle electrode 14, a battery operated neurostimulator unit 16 having a pulse generator, and a single lead wire 18 for electrically coupling the needle electrode 14 to the neurostimulator unit 16. In preferred embodiments, the neurostimulator unit 16 includes dimensions of approximately 54 mm in length, approximately 46 mm in width, and a depth of approximately 14 mm and is configured to be removeably attached to the electrode pad which is adhesively applied to a patient's skin. In other words, the neurostimulator unit 16 is sized and configured for comfortable placement of the unit adjacent the heel or ankle area of the patient.

Figure 3:
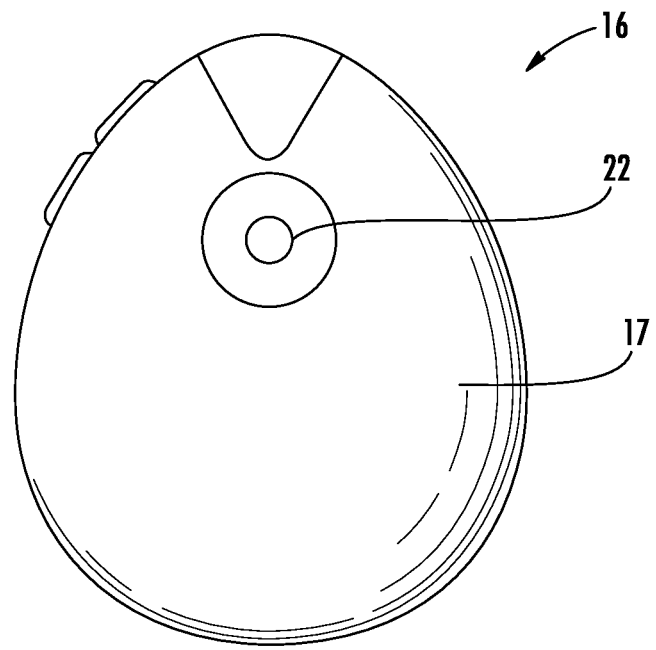
FIG. 3 is a rear view of a neurostimulator unit according to one embodiment of the disclosure.
Figure 4:
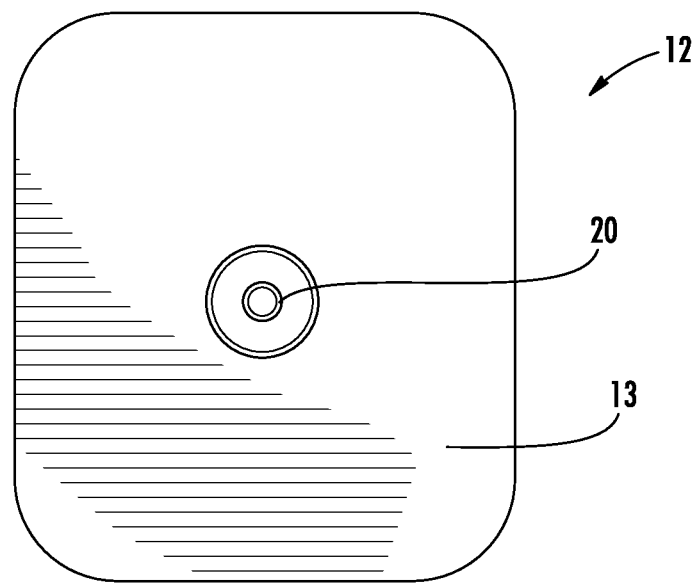
FIG. 4 is an front view of an transcutaneous electrode patch according to one embodiment of the disclosure.

Referring to FIGS. 3-4, the transcutaneous electrode pad 12 includes an attachment mechanism 20 on the top surface 13 of the pad 12 and the neurostimulator unit 16 includes a corresponding attachment mechanism 22 on the bottom surface 17 of the neurostimulator unit 16 for removeably attaching and electrically coupling the neurostimulator unit 16 with the electrode pad 12. In a preferred embodiment, the neurostimulator unit 16 includes a female snap connector 22 disposed on the bottom surface 17 that connects to a corresponding male connector 20 disposed on the top surface 13 of the electrode pad 12.

By providing a neurostimulator unit 16 having an integrated pulse generator and electrode pad 12 during operation of the stimulator device 10, only a single lead 18 is needed to be included in the device 10 to connect the needle electrode 14 and provide stimulation to the stimulation site. No lead wire is needed to electrically couple the neurostimulator unit 16 and electrode pad 12. This results in a compact system having very few parts. The entirety of the system is also able to be connected to the patient during treatment which provides the patient greater flexibility in movement during a treatment session. Further, as a hand held pulse generator is not being used, the single lead 18 only needs to be as long as the distance from where the electrode pad 12 is applied to the skin of the patient to the insertion site of the needle electrode 14.

In operation, the transcutaneous electrode pad 12 is positioned near a selected stimulation site on the surface of the skin. The percutaneous needle electrode 14 is then inserted through the skin adjacent the nerve or nerves to be stimulated, i.e., preferably adjacent the tibial nerve when treating incontinence. The neurostimulator unit 16 is attached to the transcutaneous electrode pad 12 and the lead wire 18 is connected to the neurostimulator unit 16 so that the pulse generator is electrically coupled to both the electrode pad 12 and the needle electrode 14. When the pulse generator is activated to perform a treatment session, current pulses traverse the stimulation site by passing from the transcutaneous electrode 12 to the internal percutaneous electrode needle 14.

Figure 2:
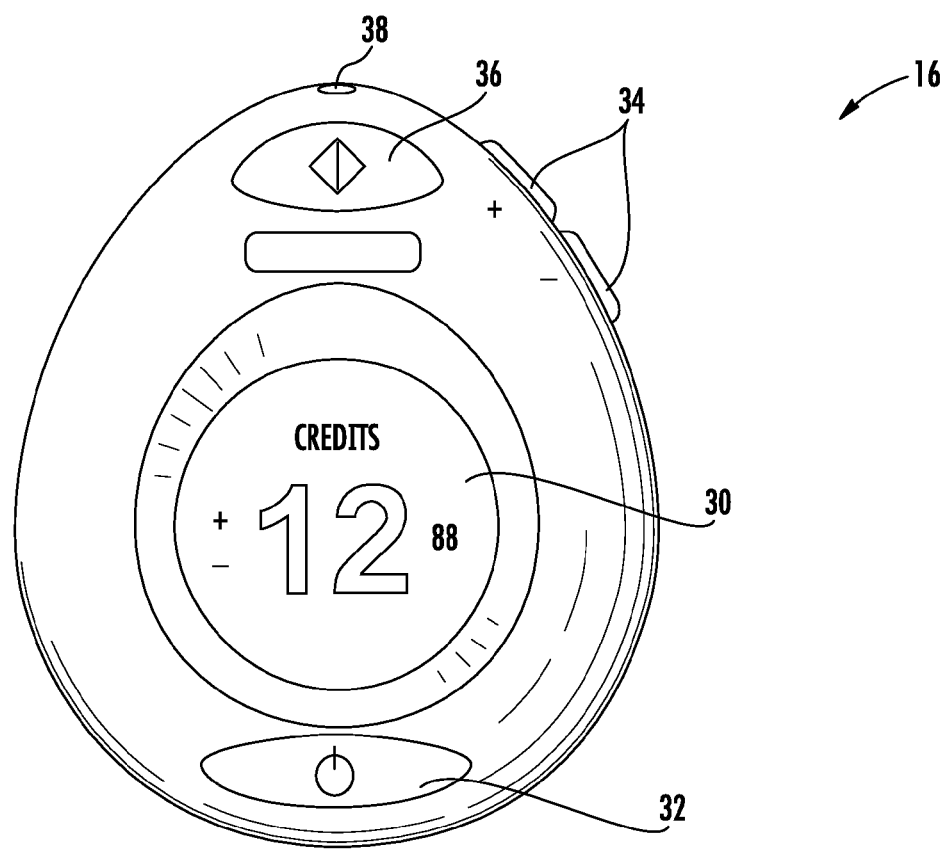
FIG. 2 is a front view of a neurostimulator unit according to one embodiment of the disclosure.

Referring to FIG. 2, the neurostimulator unit 16 includes a LCD display or other type of graphic display 30 for displaying operating information of the unit 16 such as the battery level, time remaining for a treatment session, signal strength of the pulse generator, treatment credits remaining for the unit 16, and a network/computer connection status. Further aspects of the neurostimulator unit may include, for example, operating utilities such as a power button 32 for turning the unit 16 on and off, a toggle control 34 for adjusting the signal strength of the pulse generator, a start button 36 for beginning a treatment session, and a receiver 38 for receiving the lead wire 18 and electrically coupling the percutaneous electrode 14 to the neurostimulator unit 16.

In preferred embodiments, the graphic display 30 and/or some of the operating utilities may be either removable or permanently separate from the neurostimulator unit 16 to allow for handheld control of the device 10. Such a design would provide for further compactness of the neurostimulator unit 16. The handheld unit could be a custom designed device, a smartphone app running on a smartphone or tablet computer, or software downloaded to a personal computer or accessed through the Internet. The computer/handheld unit would then preferably communicate with the neurostimulator unit 16 wirelessly using an infrared, Bluetooth, wireless Internet, or other means of wireless connection. Alternatively, the handheld unit may include a wired connection with the neurostimulator unit 16. Other features of the computer/handheld unit may include the ability to control multiple neurostimulator units 16 and the ability to time each treatment session and notify the patient or administrator with an audio alert at the end of the treatment session.

In another aspect of the disclosure, the neurostimulator unit 16 is preferably connectable to a computer system, which in turn is connected to a central server for providing a treatment credit purchasing system and for monitoring the status and usage of the device 10. The neurostimulator unit 16 is preferably operable to communicate with the computer system through a communicator that connects with a communication network. In preferred embodiments, the computer system includes a transfer device such as the handheld unit described above for facilitating communication between the neurostimulator unit 16 and the central server. As noted above, transfer device could include one or more of a personal computer, smartphone, tablet computer, etc. In these embodiments, the neurostimulator unit 16 is connected to the transfer device using, for example, a universal serial bus (USB) connector or wirelessly by using an infrared, Bluetooth, wireless Internet, cellular network or other means of wireless connection. Alternatively, information may be transferred between the neurostimulator unit 16 and the transfer device using a portable digital storage device such as a USB storage drive. In other embodiments, the communicator of the neurostimulator unit 16 connects to the communication network and central server directly without the need of a transfer device through, for example, the Internet or a cellular network.

Accordingly, the transfer device preferably incorporates memory storage for banking purchased credits, and a microcontroller for managing credit acquisition and utilized consumption (e.g., adding and subtracting from the stored credits), a display for communicating the number of stored credits and other useful information related to use, and a USB connector. The device can be attached to any computer with access to the Internet and a USB port to purchase use credits over the internet from the manufacturer/distributor/third party-payment handler and store purchased use credits authorized by the central server. The device may then be attached via USB port or wireless connection with an appropriately programmed neurostimulator unit to provide therapy based on the availability of stored credits from the transfer device.

The neurostimulator unit 16 further includes a microcontroller for storing information relating to the current status and past usage of the unit 16 and controlling operation of the device 10. The status and usage information may be transferred from the unit 16 to the computer system when the unit 16 is connected to the computer system. In particular, the microcontroller monitors a number of treatment credits the neurostimulator unit has available to it. Each available treatment credit corresponds to a treatment session or portion of a treatment session. After a treatment session is completed, the number of available treatment credits is reduced. If there are no more treatment credits available to the neurostimulator unit 16, the microcontroller prevents the neurostimulator unit 16 from performing a treatment session by preventing activation of the pulse generator. In order for the unit 16 to be used in further treatment sessions, additional treatment credits must be purchased and transferred to the neurostimulator unit 16. The concept of purchasing credits for each use is seen to be applicable to other medical devices used for medical diagnosis, medical therapy, lab testing equipment as well as corresponding devices for veterinary, dental and chiropractic applications.

Figure 5:
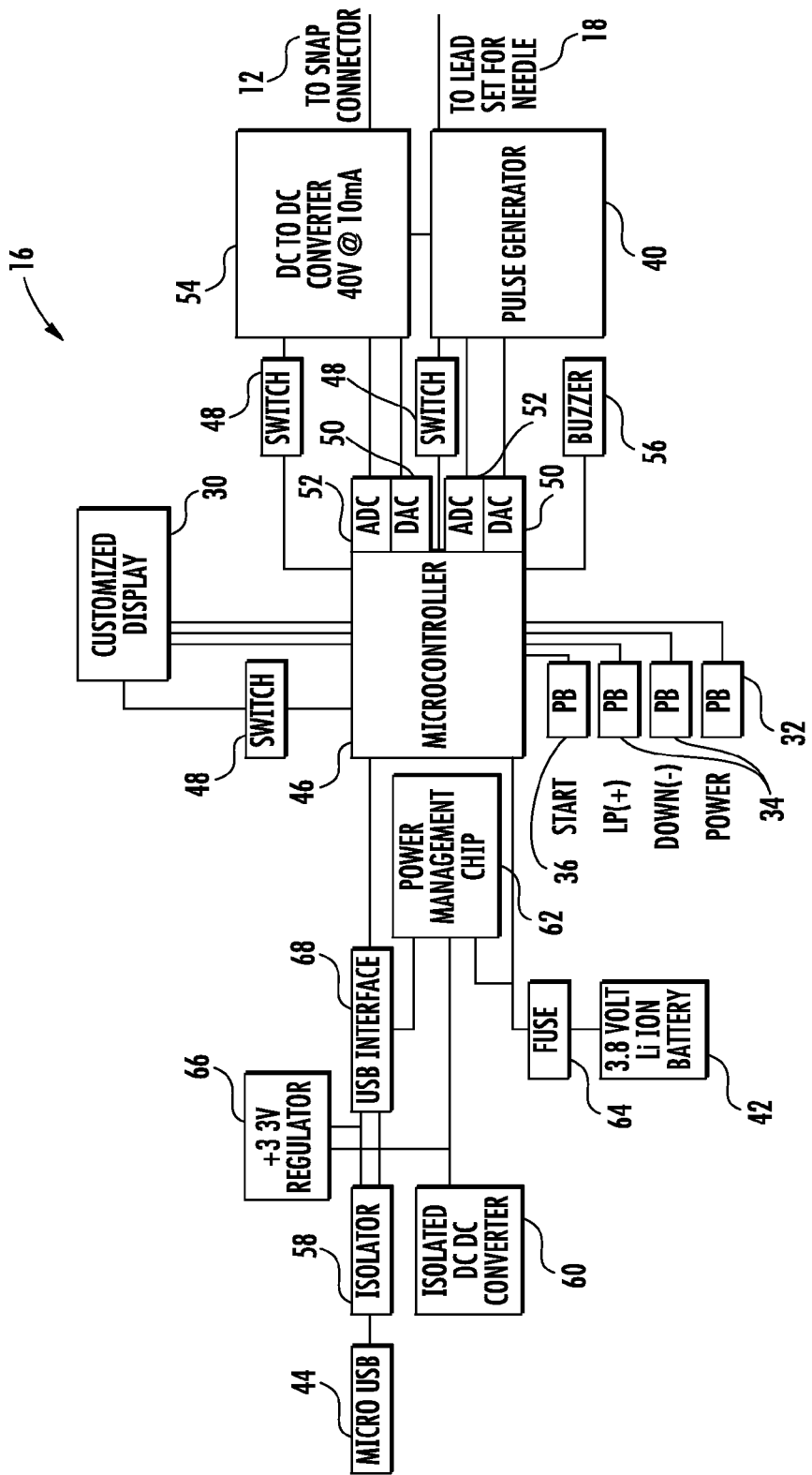
FIG. 5 is a block diagram of the internal circuitry of a neurostimulator unit according to one embodiment of the disclosure.

With reference to the block diagram of FIG. 5, one embodiment of the circuitry of the neurostimulator unit 16 is disclosed. As described above, the neurostimulator unit includes the graphic display 30, power button 32, toggle control 34, start button 36, pulse generator 40, battery 42, USB port 44, and microcontroller 46. The microcontroller 46 controls operation of the high voltage supply (DC to DC converter 54)

and display of the operational characteristics on the graphic display 30 using a series of switches 48, digital-to-analog converters 50, analog-to-digital converters 52, and a DC to DC converter 54. A warning mechanism 56 such as a buzzer or light may be provided for notifying a patient or administrator that a treatment session is completed or a problem has occurred with the neurostimulator unit 16.

As shown, it is preferred that the USB port 44 is electrically isolated from the remaining components of unit 16 using an isolator 58 and isolated DC to DC converter 60. Other aspects of the unit 16 include a power management chip 62 disposed between the battery 42 and microcontroller 46, which uses power from the USB port 44 to charge the battery 44 connected through a fuse 64 disposed between the battery 42 and microcontroller 46. A regulator 66 is provided for maintaining a constant supply voltage to the USB interface 68 when the USB port 44 is connected.

Figure 6:
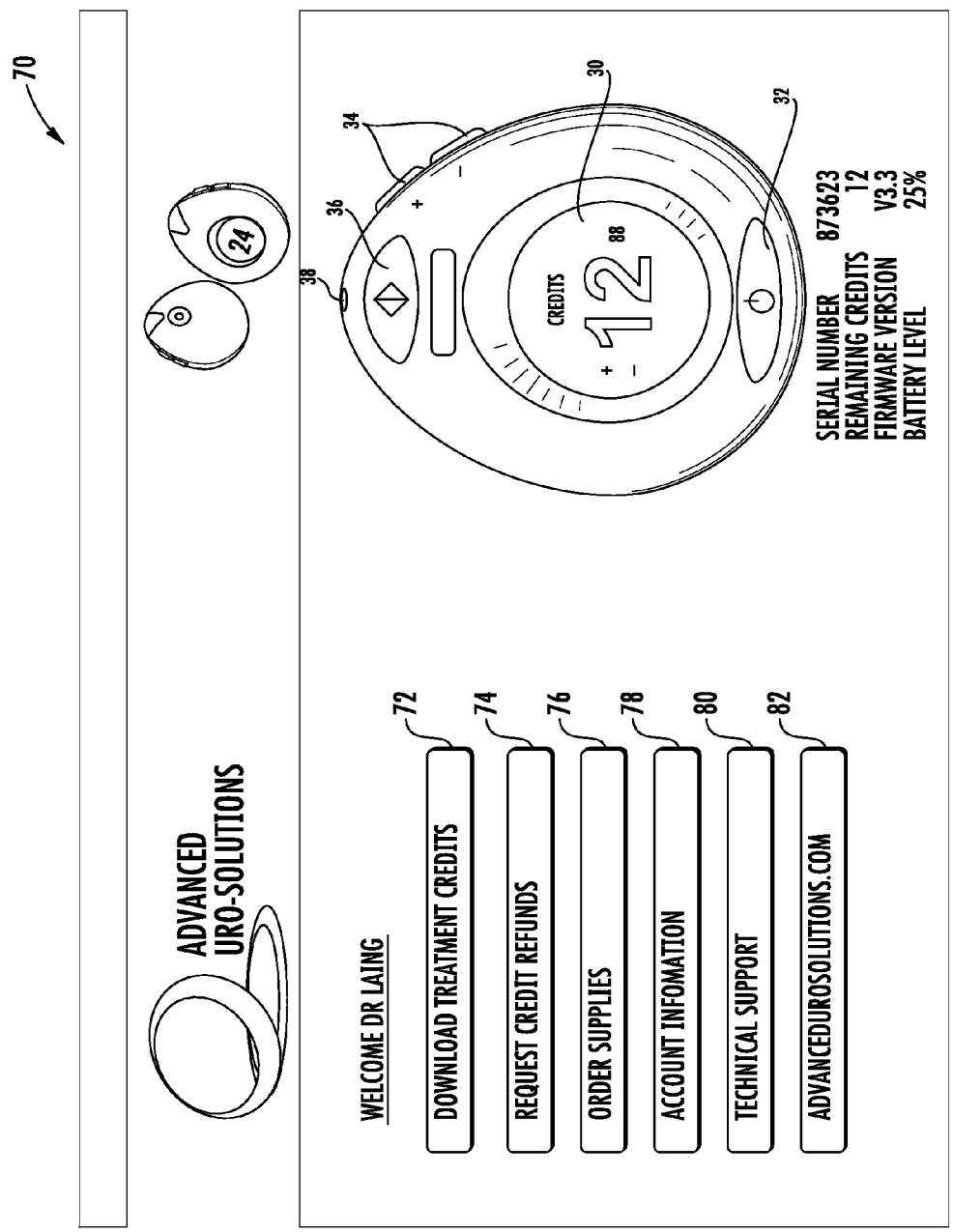
FIG. 6 is a view of a customer interface according to one embodiment of the disclosure.

Referring to FIG. 6, the computer system/transfer device includes a customer interface 70 for purchasing treatment credits to be used with an appropriate neurostimulator unit 16. It should be understood that the customer could include the patient or a health care professional or office that administers treatment sessions to patients, and the terms user, customer, patient, and administrator may be used interchangeably herein. Each customer is set up with a customer account and the customer's neurostimulator unit or units 16 are then linked to this account. The customer interface 70 is preferably available to the customer through a web-based or downloadable software application accessible from a desktop computer, laptop, tablet computer, smartphone, or the like.

As shown in FIG. 6, the customer has several options to choose from through the customer interface 70 such as downloading and purchasing treatment credits 72, requesting a refund of treatment credits 74, ordering supplies 76 such as electrode pads 12 and needle electrodes 14, accessing account information 78, requesting technical support 80, and one or more links 82 that redirect the user to additional information on the web such as the manufacturer website.

When the neurostimulator unit 16 is connected to the computer system, the microcontroller is updated, preferably automatically, based on the actions of the customer through the customer interface 70. For example, if the user purchases a treatment credit using the customer interface 70, the purchased treatment credit is transferred to the microcontroller of the neurostimulator unit 16 for providing the user with an additional treatment session when the unit 16 is connected to the computer system or a network connected to the computer system.

Figure 7:
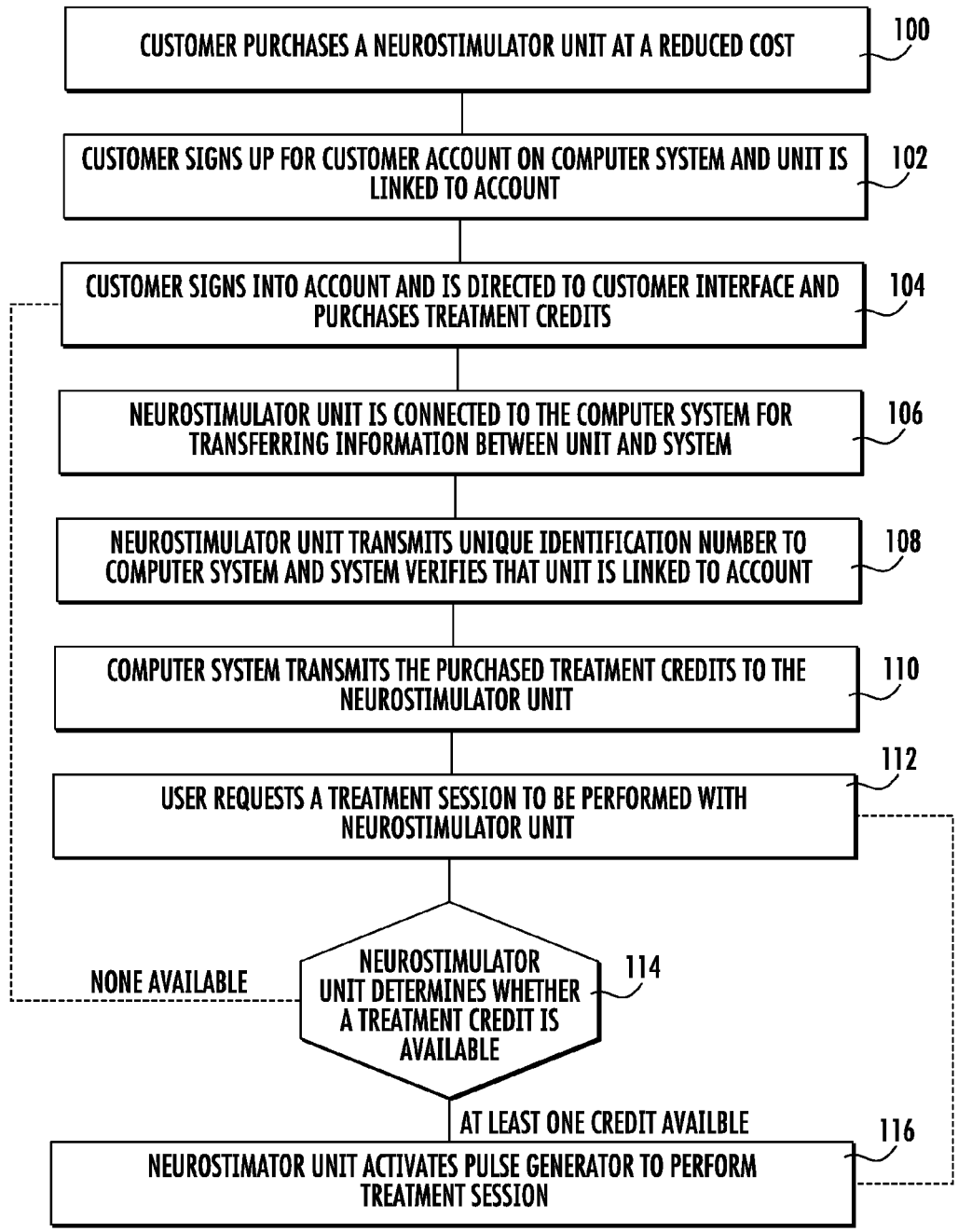
FIG. 7 is a flow chart of a method for performing treatment sessions using a neurostimulator unit according to one embodiment of the disclosure.

Referring to FIG. 7, a method for performing tibial nerve stimulation treatment sessions using the nerve stimulation device 10 is provided. It should be understood that the following steps are generally performed in no particular order and some steps may be omitted. In step 100, the user or customer is provided with a nerve stimulation device 10 having a neurostimulator unit 16 as described substantially above. Preferably, the nerve stimulation device 10 is provided to the customer at a reduced cost, which is to be recouped by having the customer pay for using the device 10 on a per-treatment session basis. In step 102, the customer signs up for a customer account on the computer system and links the customer's one or more neurostimulator units 16 with the customer account. Information submitted to computer system is transferred to the central server through the communication network for authorization. Preferably, each neurostimulator unit 16 includes a unique identification number and the neurostimulator unit 16 is linked to the customer account by providing the appropriate unique identification number.

After signing into the customer account, the customer is directed to the customer interface 70 and purchases one or more treatment credits in step 104. The purchase request is routed to central server, which authorizes the request and credits the treatment credits to the customer account. Each purchased treatment credit preferably includes a unique serial number for assisting in tracking usage of the treatment credit. In step 106, the neurostimulator unit 16 is connected to the computer system through a wireless or hardwire connection as described above for transferring information between the neurostimulator unit 16 and the computer system. In step 108, the neurostimulator unit 16 transmits its unique identification number to the computer system and the computer system verifies that the unit 16 is linked to the customer account.

After verification that the unit 16 is an authorized device for the particular customer account, the computer system transmits the one or more treatment credits purchased in step 104 to the neurostimulator unit 16 in step 110. Alternatively, the information could be transferred between the computer system and the neurostimulator unit using a digital storage device such as a flash storage drive. In addition to transmitting the purchased treatment credits to the neurostimulator unit 16, information transferred to the computer system from the neurostimulator unit 16 could include a number of remaining treatment credits, if any, available to the unit 16, the total number of treatment sessions provided by the unit 16, the status of incomplete treatment sessions performed by the unit 16, usage information of particular treatment credits based on the treatment credit's unique serial number, battery status, etc. This information can then be accessed from the customer interface 70 for monitoring the status and usage of the neurostimulator unit 16 when desired. For example, the usage information would be helpful when preparing bills to patients and processing insurance claims.

In step 112, the patient or administrator requests a treatment session to be performed using the neurostimulator unit 16. At this point, the unit may or may not be connected to the computer system. In step 114, the neurostimulator unit 16 determines whether a treatment credit is available. If it is determined in step 114 that there the unit 16 has no more available treatment credits, the patient or user must return to step 104 to purchase additional treatment credits before another treatment session may be performed. If a treatment credit is available, the nerve stimulation device 10 performs a treatment session using one of the treatment credits purchased in step 104 and transferred to the neurostimulator unit in step 116. In performing the treatment session, the unit 16 activates the pulse generator so that current pulses traverse the stimulation site during the treatment session by passing from the transcutaneous electrode 12 to the internal percutaneous electrode needle 14. After a treatment session is performed, the number of available treatment credits is reduced by one. Step 112 is then repeated when another treatment session is requested.

In certain embodiments, the above treatment credit system may be replaced or supplemented with a post-paid type service where the user is billed according to a predetermined time period. based on the number of treatments sessions performed by the device during the payment period. Each device is awarded a certificate for the future use period. It should be understood that the certificate is similar to the treatment credits described above except that it has a time duration as opposed to be limited to one particular treatment session. The device has the capability of counting uses in the time period. At the end of the time period, the certificate expires. Connecting to the central server, such as through a vendor's website or software application, allows the owner to upload to the central server the uses of the last time period, arrange for payment, and download a certificate for the future defined period that may be moved to the device by a transfer device described earlier. As noted above, in this embodiment, the microcontroller of the neurostimulator unit 16 continues to store information relating to past usage of the unit 16 for controlling operation of the device 10. Further, the pulse generator may be activated so long as an unexpired use certificate is available. Devices that are capable of remaining connected to the central server, such as through an Internet or cellular connection, may also be monitored in real time by the vendors commerce site and regular billing for each use can be carried out without a transfer device.

In preferred post-treatment payment embodiments, the user may be given an unpaid credit limit equal to a number of allowed unpaid (i.e., postpaid) uses in addition to or in replacement of the requirement to prepay for all treatment credits. Upon a treatment session request, the microcontroller first determines whether the user has any prepaid treatment credits available (if applicable). If none are available, the microcontroller then determines whether the user has exceeded its unpaid credit limit if an unpaid credit limit has been given to the user. It should be understood that the unpaid credit limit could have a time duration, such as by incorporating the unpaid credit limit with a time certificate as described above. If the user's unpaid credit limit has not been reached, the pulse generator is activated and a treatment session is performed. On the other hand, if the user's unpaid credit limit has been reached, the user must access their account and pay off/down their balance owed and/or purchase prepaid treatment credits. Following payment, the user may then connect the neurostimulator unit 16 to the central server to reset the device's unpaid credit limit or update the amount of prepaid treatment credits stored to the device. Thus, the advantage of providing the user with an unpaid credit limit is that the neurostimulator unit 16 does not have to be connected to the central server each time prepaid credits are exhausted and a treatment session request is made.

In other words, when an unpaid credit limit is given to the customer or a customer account, the unpaid credit limit provides a number of treatment credits be made available to the "credit exhausted" customer account without the immediate need for access to the web commerce site of the vendor. When a treatment session is performed on an unpaid credit, the number of unpaid treatment credits available to the device is reduced. Similarly, when a prepaid treatment session/credit is transferred from the customer account storage to the medical device, the number of prepaid credits transferred is reduced by the number of used, unpaid treatment credits recorded and the account unpaid credit limit is appropriately restored. Similarly, once payment is provided for the unpaid treatment sessions already performed, credit is restored and the number of unpaid treatments credits available to the customer account is increased up to the unpaid credit limit.

Figure 8:
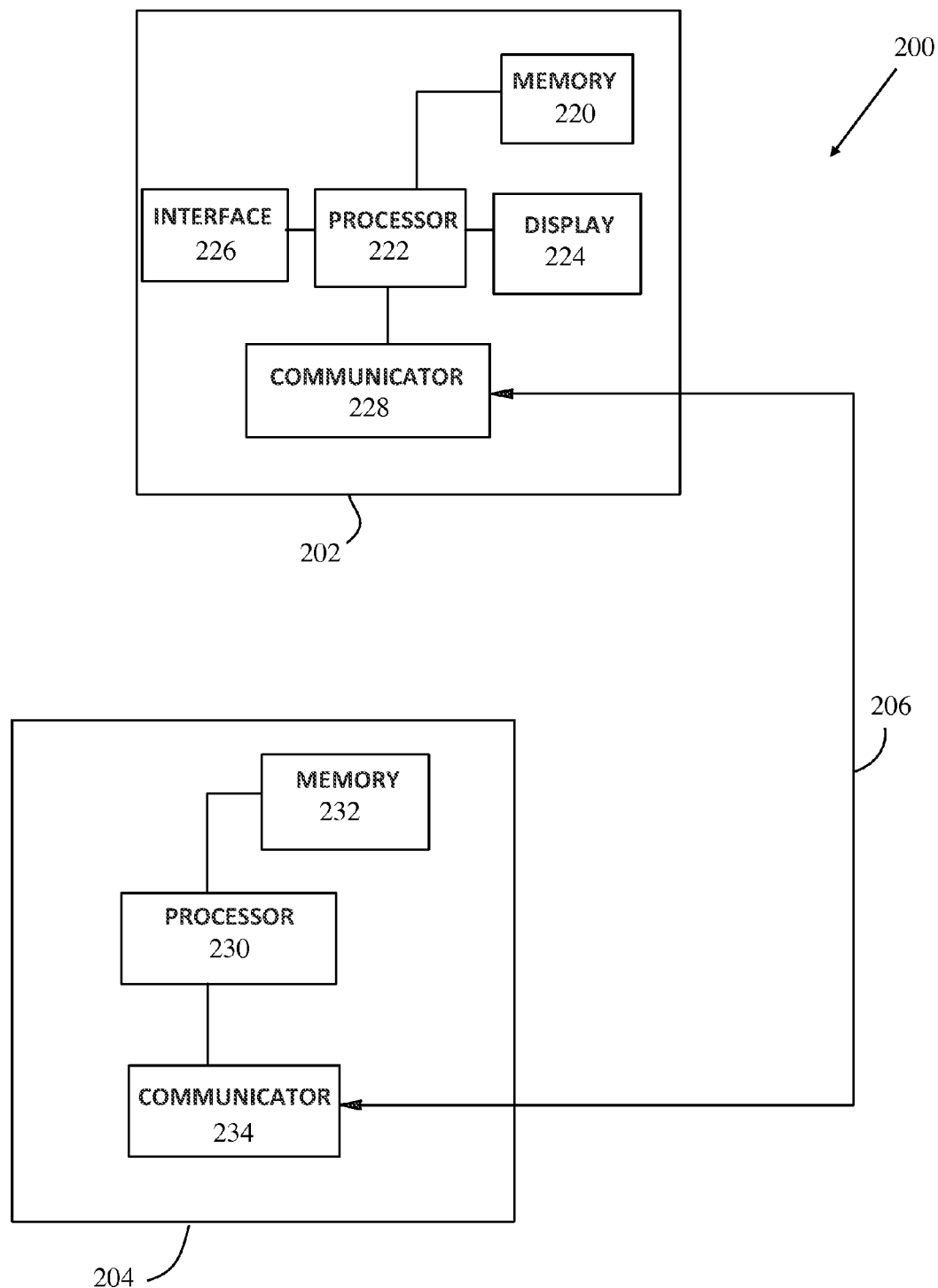
FIG. 8 is a schematic diagram of a medical device and central server of a payment system according to one embodiment of the disclosure.

As noted above, the payment system described above with respect to a nerve stimulation system is applicable to other medical devices, particularly those in the dental, veterinary, and chiropractic fields. Referring to FIG. 8, a payment system 200 implemented substantially as described above for other medical devices is schematically shown having a medical device computing unit 202, a central payment server 204, and a communication network 206 connecting the medical device 202 to the central server 204. In preferred embodiments, the payment system 200 includes a plurality of medical devices 202 operable to be connected to the central server 204. Each of the plurality of medical devices 202 includes a memory 220, processor 222, and communicator 228. The processor 222 functions similarly to the microcontroller described above in that stores usage data at memory 220 and controls functioning of the device based on the usage data and/or communication of the unit 202 with the central server 204. The central payment server 204 also includes a processor 230 connected to a memory 232 and a communicator 234. Communicator 228 of medical device 202 and communicator 234 of central server are operable to transmit and receive information between each other through communication network 206.

As explained above in the example of a nerve stimulator device, the communicator 228 in certain embodiments is operable to directly connect to the central server 204 using a wired or a wireless connection such as cellular, Bluetooth, or wireless Internet connection. In this embodiment, the medical device preferably includes a display 224 and interface 226 as shown for displaying and entering operating information for device 202. In preferred embodiments, a transfer device such as a smartphone, USB storage device, laptop, tablet computer, or similar computing device having an associated memory for downloading, storing, and transmitting treatment credits and usage data is used to transfer information between the medical device 202 and central server 204. According to this embodiment, communicator 228 is operable to transmit and receive information from the central server 204 by connecting the medical device 202 to the transfer device.

The foregoing description of preferred embodiments for this disclosure have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of providing payment for use of a medical device on a per-treatment session basis, the method comprising:

providing a customer computer system having a customer interface;

providing a medical device computing unit including a microcontroller for monitoring a number of treatment sessions available to the medical device and for activating the medical device when the number of treatment sessions available is at least one, the number of treatment sessions available determined based on at least one of a credit limit provided to the customer for postpaid treatment sessions and a number of prepaid treatment credits purchased by the customer;

receiving a treatment credit request transmitted through the customer interface, the treatment credit request having purchase information including at least one of payment of a number of postpaid treatment sessions already performed and payment for a number of prepaid treatment credits;

transmitting the treatment credit request from the customer computer system to a central payment server for validation;

receiving at the customer computer system validation information, the validation information corresponding to at least one of the number of postpaid treatment sessions paid for and the number of prepaid treatment credits purchased;

connecting the microcontroller of the medical device computing unit to the customer computer system;

transmitting the validation information from the customer computer system to the microcontroller; and adjusting the number of treatment sessions available to the medical device based on the validation information.

2. The method of claim 1 further comprising:
determining whether the number of treatment sessions available is at least one; and
activating the medical device based on a treatment session request when it is determined that the number of treatment sessions available is at least one.

3. The method of claim 1 further comprising:
transmitting usage information from the microcontroller to the customer computer system, the usage information including a number of treatment sessions performed;
monitoring the usage information of the medical device through the customer computer system; and
providing the usage information to the customer through the customer interface of the customer computer system.

4. The method of claim 1 wherein the microcontroller communicates with the customer computer system through one of radio frequency, Bluetooth, infrared, and a wireless Internet connection.

5. The method of claim 1 wherein the microcontroller communicates with the customer computer system through a universal serial bus connection.

6. The method of claim 1 wherein the medical device includes the customer interface of the customer computer system and a communicator to communicate directly with the central payment server.

7. A method of providing payment for use of a medical device on a per-treatment session basis, the method comprising:
providing a customer computer system having a customer interface;
linking the medical device to a customer account, the customer account for monitoring a number of treatment sessions available to the customer account;
providing a medical device computing unit including a microcontroller for monitoring usage information directed to a number of treatment sessions performed by the medical device, for updating a number of treatment credits available to the medical device based on the number of treatment sessions performed by the medical device, and for activating the medical device upon a treatment session request when the number of treatment credits available to the medical device is at least one;
connecting the medical computing unit to the customer computer system for transmitting at least one of the number of treatment sessions available to the customer account to the microcontroller, each of the number of treatment sessions available transmitted to the microcontroller corresponding to one treatment credit available to the medical device; and
updating the number of treatment credits available to the medical device based on the number of treatment sessions available to the microcontroller transmitted from the customer account.

8. The method of claim 7 further comprising receiving a treatment credit request transmitted through the customer interface, the treatment credit request including payment for a number of prepaid treatment credits, each prepaid treatment credit corresponding to one treatment session available to the customer account.

9. The method of claim 7 wherein the linking step further includes linking a credit limit to the customer account, the credit limit providing a number of postpaid treatment credits available to the customer account, each postpaid treatment credit corresponding to one treatment session available to the customer account.

10. The method of claim 9 further comprising:
receiving payment information including payment of at least a portion of the postpaid treatment credits; and
updating the number of treatment sessions available to the customer account based on the payment information.

11. The method of claim 7 further comprising:
transmitting the usage information from the microcontroller to the customer computer system;
monitoring the usage information of the medical device through the customer computer system; and
providing the usage information to the customer through the customer interface of the customer computer system.

12. The method of claim 7 wherein the microcontroller is connected with the customer computer system through one of radio frequency, Bluetooth, infrared, and a wireless Internet connection.

13. The method of claim 7 wherein the microcontroller is connected with the customer computer system through a universal serial bus connection.

14. The method of claim 7 wherein the medical device includes the customer interface of the customer computer system.

15. A method for providing payment for use of a medical device on a per-treatment session basis, the method comprising:
providing a computer system having a customer interface and a central payment server;
linking the medical device to a customer account;
providing the medical device with a medical device computing unit including a microcontroller for monitoring usage information directed to a number of treatment sessions performed by the medical device and a communicator for communicating with the computer system;
providing a user with a time certificate having an expiration date, the time certificate operable to be transmitted to the microcontroller, and the microcontroller operable to be activated upon an activation request based on the expiration date of the time certificate;
receiving at the computer system the usage information from the medical device computing unit;
billing the customer account for the number of treatment sessions performed by the medical device; and
updating the expiration date of the time certificate based on receiving payment for the number of treatment sessions performed by the medical device.

16. The method of claim 15 wherein the microcontroller communicates with the customer computer system through one of radio frequency, Bluetooth, infrared, and a wireless Internet connection.

17. The method of claim 15 wherein the microcontroller communicates with the customer computer system through a universal serial bus connection.

18. The method of claim 15 wherein the medical device includes the customer interface of the customer computer system and a communicator to communicate directly with the central payment server.

* * * * *